(12) United States Patent
McArdle et al.

(10) Patent No.: US 10,322,861 B2
(45) Date of Patent: Jun. 18, 2019

(54) DISPLAY PACKAGE FOR 2 COMPONENT CYANOACRYLATE COMPOSITIONS

(71) Applicant: AFINITICA TECHNOLOGIES, S. L., Cerdanyola del Vallès (ES)

(72) Inventors: Ciaran McArdle, Cerdanyola del Vallès (ES); Arnau Pejoan Jiménez, Cerdanyola del Vallès (ES); Carles Oriol Margarit, Cerdanyola del Vallès (ES)

(73) Assignee: AFINITICA TECHNOLOGIES, S.L., Cerdanyola del Vallès (ES)

( * ) Notice: Subject to any disclaimer, the term of this patent is extended or adjusted under 35 U.S.C. 154(b) by 0 days.

(21) Appl. No.: 15/569,131

(22) PCT Filed: Feb. 4, 2016

(86) PCT No.: PCT/IB2016/050579
§ 371 (c)(1),
(2) Date: Oct. 25, 2017

(87) PCT Pub. No.: WO2016/174529
PCT Pub. Date: Nov. 3, 2016

(65) Prior Publication Data
US 2018/0111737 A1    Apr. 26, 2018

(30) Foreign Application Priority Data
Apr. 28, 2015  (EP) .................................. 15382211

(51) Int. Cl.
*B65D 25/08* (2006.01)
*B65D 73/00* (2006.01)
(Continued)

(52) U.S. Cl.
CPC ......... *B65D 75/366* (2013.01); *B65D 5/4204* (2013.01); *B65D 81/325* (2013.01); *C07C 255/23* (2013.01); *C09J 4/06* (2013.01)

(58) Field of Classification Search
CPC .. B65D 5/4204; B65D 75/366; B65D 81/325; A61C 5/62; A61C 5/64; A61C 9/0026; C07C 255/23; C09J 4/06
(Continued)

(56) References Cited

U.S. PATENT DOCUMENTS

| 3,869,062 A | 3/1975 | Jaeschke et al. |
| 4,159,570 A * | 7/1979 | Baskas ................. A61C 9/0026 206/222 |

(Continued)

FOREIGN PATENT DOCUMENTS

| DE | 3938811 A1 | 5/1991 |
| WO | 2011143785 A1 | 11/2011 |

OTHER PUBLICATIONS

International Search Report dated Apr. 19, 2016 of corresponding International application No. PCT/IB2016/050579; 4 pgs.

*Primary Examiner* — Luan K Bui
(74) *Attorney, Agent, or Firm* — Maier & Maier, PLLC

(57) ABSTRACT

A display package for two component cyanoacrylate compositions. The display package includes a stain-free transparent secondary package that enables visual inspection of a syringe-based primary package containing a bulk product that has volatile constituents such as a common cyanoacrylate adhesive.

10 Claims, 4 Drawing Sheets

(51) Int. Cl.
  *B65D 75/36*  (2006.01)
  *B65D 81/32*  (2006.01)
  *B65D 5/42*   (2006.01)
  *C07C 255/23* (2006.01)
  *C09J 4/06*   (2006.01)

(58) Field of Classification Search
  USPC .............. 206/219, 220, 461; 433/90; 604/89
  See application file for complete search history.

(56) References Cited

U.S. PATENT DOCUMENTS

| | | | | |
|---|---|---|---|---|
| 4,166,533 | A | * | 9/1979 | Maitland ............... A61M 5/002 |
| | | | | 206/366 |
| 4,366,919 | A | | 1/1983 | Anderson |
| 4,581,023 | A | * | 4/1986 | Kuntz ..................... A61M 5/24 |
| | | | | 604/234 |
| 4,974,756 | A | * | 12/1990 | Pearson ............... B65D 41/165 |
| | | | | 222/137 |
| 2006/0255062 | A1 | | 11/2006 | Muenzenberger et al. |
| 2010/0010436 | A1 | * | 1/2010 | Wang ................... B65D 81/325 |
| | | | | 604/89 |
| 2011/0295212 | A1 | * | 12/2011 | Greter ............. A61B 17/00491 |
| | | | | 604/191 |
| 2012/0175384 | A1 | * | 7/2012 | Greter ..................... A61M 5/19 |
| | | | | 222/137 |
| 2014/0013718 | A1 | | 1/2014 | Maasarani |

\* cited by examiner

DISPLAY PACKAGE FOR 2 COMPONENT CYANOACRYLATE COMPOSITIONS

TECHNICAL FIELD

The present invention relates to a display package for 2 component (2K) cyanoacrylate based adhesive compositions.

TECHNICAL BACKGROUND

Consumers demand value for money and purchase decisions are affected by the appearance of a product and its quality. The display of products in so-called blister, bubble or clamshell packages is common for different classes of consumable goods.

Blister packs are most often the secondary packages for a further primary package held within, however for items such as electrical cables, some computer accessories, food products, and so-forth, the blister or clamshell pack itself is the only package. In any case, blister packs enable the consumer to see and appreciate the product inside and inspect it. If the blister package were soiled or stained internally in an unsightly manner, this would invariably affect the consumer's decision to buy the product, as the product would appear defective.

Cyanoacrylate (CA) adhesives, or so-called superglues, are popular consumer goods. Cyanoacrylate is the generic name for a family of resistant fast acting adhesives based on esters of 2-cyanoacrylic acid. The structure of the monomer is as follows:

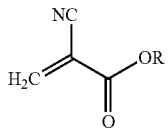

wherein R is usually an alkyl group such as, for example, methyl, ethyl, butyl, or octyl, or an alkoxyalkyl group, for example, 2-methoxymethyl or 2-ethoxyethyl.

Such compounds have been well known for some time, as described in, for example, S. Ebnesajjad Ed., *Adhesives Technology Handbook*, William Andrew, Norwich, 2008.

In many industrial and domestic applications CAs are used in form of one-component, as they polymerize rapidly when they are in the form of a thin film between two substrates in the presence of anions or nucleophilic species. The speed at which the bond is formed and the ease of use have contributed to their popularity. For other applications CAs are used in form of two components, one component containing the CA and the other a composition comprising plasticizer and catalyst, or a non-CA polymerisable monomer mixture and a catalyst. These 2K CA adhesives show high technical performance characteristics.

One-component CAs are sold in various types of primary packages most commonly in bottles or aluminium tubes. Such packs are usually subsequently contained in secondary packaging such as foldable boxes, or in blister packs. The moisture sensitive nature of these very reactive adhesives necessitates that the primary package is tightly closed by a removable cap for bottles, or a membrane seal for tubes as disclosed, for example, in International patent applications WO-A-99/44907, WO-A-01/56894, WO-A-2005/075312, and WO-A-2007/004203. This current packaging method is essential for all CA based adhesives irrespective if they are known to emit vapours or not.

The problem of vapour emission from common one-component CA based adhesives and the staining it causes, has heretofore not been encountered in blister packs containing these traditional hermetically sealed primary packages when the products are first displayed. That staining is known as 'blooming' or chlorosis, and it is disclosed, for example, in the British patent application GB-A-2067553.

More recently so-called two-part, two-component or 2K, cyanoacrylate adhesives have appeared in the marketplace. Whereas the concept of 2K CAs is well known in the prior art, as disclosed, for example, in U.S. Pat. No. 3,282,773, they have only emerged as articles of commerce recently and in double-barrelled syringes that are used as primary packages, for example, Loctite 3090, Loctite 3092, Loctite 4090, Afinitica Super Repair, Afinitica Soldadura Adhesiva, or Afinitica Soldadura Adhesiva Metal.

To date such syringes are most usually contained in foldable boxes that do not allow the product to be visible. However, one such product, Loctite 3092, has been commercialized using a semi-transparent plastic bag as a secondary package. White staining on the inside of the aforementioned plastic bag is evident in that case and detracts from the appearance of the product.

The problem arises because the CA adhesive contains a monomer constituent that has a high vapour pressure. Common CA monomers, such as alkyl CAs, and in particular ethyl cyanoacrylate (ECA) are known to have high vapour pressure, be lachrymatory and irritant in nature and have product labelling to indicate this fact. The syringe package format containing such CAs is not hermetically sealed. Whereas the syringe format for 2K CAs has a tightly fitting re-closable cap at the dispense orifice end (proximal end), its base is movable by virtue of a snug-fitting piston located within syringe barrels. The product is confined between the piston and the proximal end of the syringe. Such 2K CA products are most commonly of a gel consistency and the snug-fitting piston confines the bulk product well.

Although pistons in syringes may be considered to confine ECA based bulk compositions in good condition, they cannot retain emissive vapours issuing from the bulk product since vaporized molecules easily pass non gas-tight parts. This phenomenon creates a significant specific problem uniquely when presenting syringe based ECA products in transparent blister packs because the vapours polymerise inside the blister bubble and manifest as an unsightly white stain. This staining creates the impression of a defective product and influences purchasing decisions by consumers. On the other hand, this very staining feature of common CAs is used to advantage in unrelated applications and they are materials of choice for the visualization of fingerprints in forensic science.

In the case of syringes containing a CA composition, the piston must move during product dispensing and, thus, a small but finite gap exists between the walls of the syringe barrel and the piston element itself. Furthermore, because CAs are such effective adhesives, the pistons in these syringes do not employ deformable O-rings to seal finite gaps because the latter become glued to the container walls and lock.

This piston-stick problem was identified in the prior art and a solution was proposed in U.S. Pat. No. 5,016,784 by use of hydrocarbon grease disposed between a non-stick polymeric seal and a CA adhesive contained in a syringe barrel. Thus the grease was in direct contact with the CA adhesive. This grease aids smooth advancement of the plunger (piston) in the barrel. This alternative solution proposed specifically for single-barrelled CA syringes, creates significant problems for mass production in the case of double-barrelled syringes for the recently commercialised 2K CAs. Before filling, the pistons in each of the two barrels in a 2K empty syringe are inserted and pushed to the proximal end to a position above the orifices. The adhesive part (so-called Part A) and the catalyst-plasticizer, or catalyst-non-CA monomer mixture part (so-called part B) are simultaneously pumped into the respective syringe barrels through the individual orifices under pressure to fill the chambers of the syringes in an operation that also forces the pistons back into their ultimate final position which is intermediate along the length of the syringe. The technical solution of the '784 patent, when applied to a double-barrelled syringe, implies that the hydrocarbon grease would have to be first introduced into the barrel before either product part in a separate operation and also must be introduced in both chambers so the pistons rise up to the same position in each chamber to ensure subsequent proper dispensing from the double plungers supplied with double-barrelled syringes which have equal plunger lengths. Compatibility of hydrocarbon grease with plasticizers and catalysts is not foreseen in the '784 patent, which is addressed to a single component product. Furthermore, due to the special design described in the '784 patent, the syringe requires an end-stop within the barrel to prevent final discharge of the hydrocarbon grease, which is an 'anti-adhesive', and a significant air gap is formed between the greased piston in the stopped position and the orifice as illustrated in FIG. 3 of that US patent. That situation would be amplified twofold if applied to a 2K CA syringe and such included air pockets would generate serious problems in uniform dispense and mixing of a 2K CA product. Those problems are not anticipated in a single-barrelled syringe. In fact and by default, compositions suited to single-barrelled syringes do not require mixing during dispense unlike those from double-barrelled syringes, which require uniform mixing of the CA and the catalyst. The mixing of components of compositions is thus unique to 2K CA syringes and the solution proposed by the '784 patent to prevent piston-stick, is not practical for 2K CA syringe design, end use, or for their filling in mass production.

Another approach is selling 2K CAs in a foldable box. In that case the problem is concealed, but still exists. However there is no initial negative impact on the customer unless the box is opened. On the other hand, the advantage of allowing a customer to directly examine the product for purchase is forgone.

Lastly, many patents have detailed the design of 2K syringes and their intricate components, as disclosed in, for example, US Patent Application US-A-2013/0177870, International patent applications WO-A-2005/075312 and WO-A-2006/005206, and European patent application EP-A-0730913, especially with particular attention to the design of securely sealing the syringes, for example, with special re-closable caps for the orifice (proximal) end.

However no consideration has been directed to problems regarding the holistic quality of display package containing piston-sealed syringes comprising products with volatile constituents that cannot avail of O-rings on pistons.

There is, thus, an urgent need to provide a corrective, cost effective, and industrially easy-to-implement solution to the packing of 2K CA syringes that contain volatile CA constituents. Aside from creating marketing appeal and visibility of a product, a further rationale for use of blister packaging is to reduce cost so that a solution to the problem should be realized using commercially available syringes rather than specially designed ones with internal end-stops to prevent exudation of anti-adhesive materials such as greases at any time during product use.

OBJECT OF THE INVENTION

The object of the present invention is a display package for 2K cyanoacrylate compositions.

BRIEF DESCRIPTION OF DRAWINGS

Particular embodiments of the present invention by way of non-limiting examples are described with reference to the accompanying drawings, in which.

DETAILED DESCRIPTION OF THE INVENTION

Figure 1:
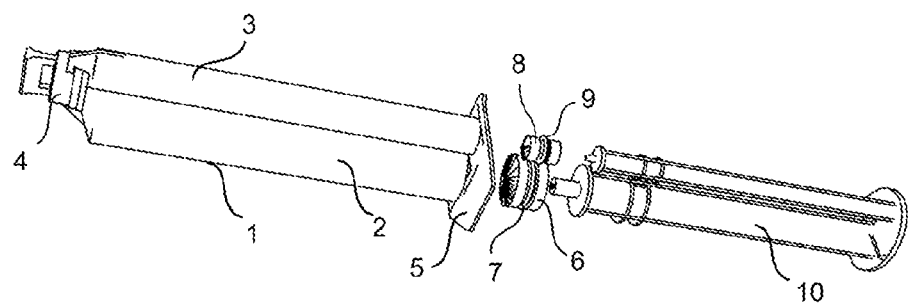
FIG. 1 illustrates schematically a double-barrelled syringe of the type used in the present invention.

The object of the present invention is a display package for 2K cyanoacrylate compositions comprising:
a) a secondary outer pack,
b) a primary inner pack, which is a double-barrelled syringe that contains:
    a. a bulk composition comprising:
        i. Part A: a cyanoacrylate based adhesive composition, and
        ii. Part B: a composition comprising a mixture of plasticizer and catalyst or a mixture of non-CA monomer and catalyst,
    b. two distinct physical parts and
    c. temporary sealing means,
c) a plunger, and
d) optionally one or more mixing elements,
wherein
    the two distinct physical parts contact the bulk composition or its constituents,
    the first physical part located at one end of the primary pack is a removable cap which closes an orifice or orifices from where bulk composition is dispensed,
    the second physical part at intermediate position within the primary pack is a group of two movable pistons which contact and confine the bulk composition between itself and the end of the pack where the orifice or orifices are located, and, temporary sealing means, which forms a barrier between volatile constituents emitted by the bulk composition and the outer secondary pack, and which means is located between the second physical part and the distal end of the syringe.

By insertion of an additional temporary barrier between the secondary outer pack and the movable piston parts of a primary inner package contained within the former, the authors of the present invention have discovered a pragmatic solution to a problem that can influence a customer purchase decision, which is highly practical to implement in industrial scale manufacturing of filled 2K CA syringes.

In the present description as well as in the claims, the singular forms "a" and "an" include also the plural reference unless the context clearly indicates otherwise.

Display Package

The display package of the present invention comprises a primary inner pack, a secondary outer pack, a plunger and, optionally, one or more mixing elements.

The secondary outer pack of the display package is a foldable box, a blister, a bubble, a clamshell pack, or a bag. The blister, bubble or clamshell pack is collectively referred to as a blister package.

The secondary outer pack is described along with its content components in more detail below and by reference to the schematic representation in FIG. 7. The display pack may be free standing if the secondary outer pack forms a stand, or may have a hook-hole to allow the display to be hung on a hook.

The primary inner pack inside the secondary outer pack is a double-barrelled syringe, as shown, for example, in FIGS. 1 and 2, and which is described in more detail below complete with its additional components.

The plunger normally is not inserted into the syringe when filled. It is inserted before use and it forces the pistons in the direction of the mixing element to obtain the adhesive composition, as shown in FIG. 2.

One or more mixing element(s) may be included in the display package.

Secondary Outer Pack

The secondary outer pack of the display package is a foldable cardboard box, a blister, bubble, clamshell pack, or a bag. The blister, bubble or clamshell pack is collectively referred to as a blister package.

In a preferred embodiment the secondary outer pack is transparent or has at least one transparent section, so that the primary pack contained within can easily be visibly inspected without opening the secondary pack.

In a preferred embodiment the secondary outer pack is a blister package or a bag, and more preferably is a blister package.

In a preferred embodiment the secondary outer pack is a foldable cardboard box with a transparent plastic viewing panel.

Figure 7:
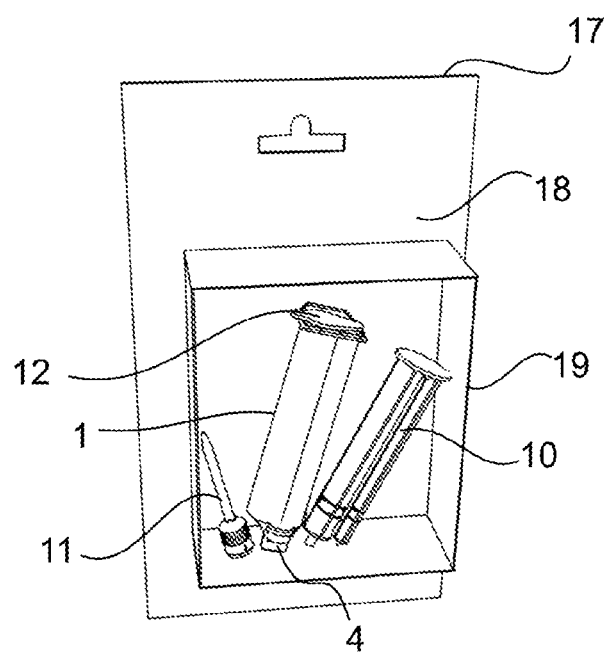
FIG. 7 illustrates a display pack comprising a secondary blister pack with a primary pack contained within, in the form of a double-barrelled syringe, where the syringe has a temporary sealant means.

Blister packages are generally made from thermoformable transparent plastics and may take the form of a transparent enclosure adhered directly to a backing card, FIG. 7, item 18. This backing card displays usually information on one or both sides about the composition or product in the primary inner pack, instructions how to use the product, applications of the product, safety information, etc.

A schematic representation of the secondary outer pack is shown in FIG. 7, item 17, and the transparent enclosure of a blister package is represented schematically in FIG. 7 by item 19. Alternatively the thermoformed plastic completely encases an information card as well as the primary inner pack. The secondary outer pack may also be a box with a viewing window, or, a sealed transparent plastic bag. The primary inner pack, item 1, complete with removable cap, item 4, is located within the secondary outer pack together with mixing element(s), item 11, and a plunger, item 10, as illustrated in FIG. 7. In FIG. 7 the temporary sealing means, item 12, is an additional cap and it is described below. In general, primary inner pack components may be lose in a blister pack or bag, or else be presented in an organized way, in the case of thermoformed blister or clamshell packs only, when components are mounted and held by shapes moulded into the plastic casing, item 19 in FIG. 7.

Primary Inner Pack

In the context of the present invention, the proximal end of the primary inner pack is taken to mean the end of the syringe from where the composition is dispensed via an orifice or orifices; and the distal end of the primary inner pack is taken to mean the extreme end of the primary inner pack farthest from the proximal end; intermediate position is taken to mean a position within the primary inner pack between the proximal and distal ends.

In the present invention, the primary inner pack is a double-barrelled syringe. Such syringes are commercially available, for example as Sulzer Mixpac K-series kits (Sulzer AG). These K-series kits are available in different sizes, e.g. 10 mL, 50 mL, and larger.

By reference to FIG. 1, the smaller size kit (10 mL) comprises syringe body, item 1, having two chambers: item 2 for adhesive Part A and item 3 for plasticizer-catalyst or non-CA monomer mixture—catalyst Part B; two pistons, items 6 and 8, with or without, O-rings, items 7 and 9, for the respective two chambers, a double plunger of a specific length (plunger), item 10, and a removable or re-closable cap, item 4, at the proximal end. The syringe body, item 1, is fashioned with finger-pull flaps, item 5, for ease of handling at the distal end. Normally the plunger is not inserted into the syringe when filled and the pistons are at an intermediate position in the syringe body between the proximal and distal ends. When the syringe is full of composition, the pistons are located quite close to the distal end. The volumetric ratio of syringe chambers, items 2 and 3, are available as 1:1. 2:1, 4:1, 10:1 (A:B) ratios. Larger syringe sizes (e.g. 50 mL) do not have finger pull flaps, but have a flat flange designed to fit into a dispensing gun accessory that has its own plunger mechanism.

Figure 2:
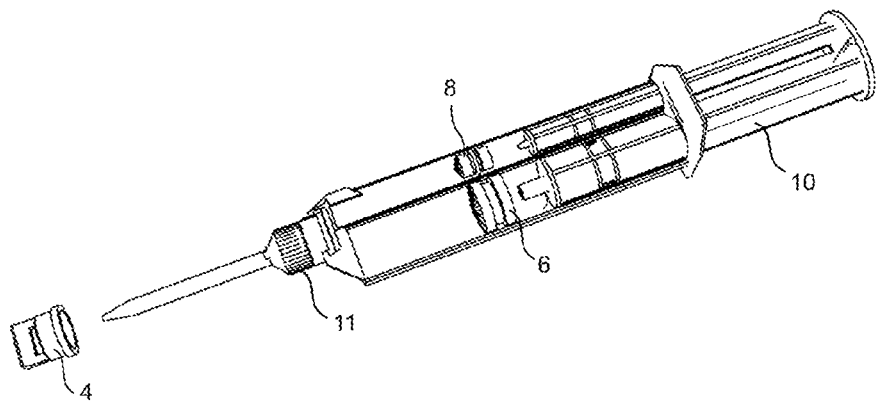
FIG. 2 presents an alternative cut-away view of a double-barrelled syringe of the type used in the present invention illustrating insertion of syringe plunger into distal ends, intermediate position of syringe pistons and the position of a mixing element in place of a removable or re-closable cap.
Figure 3:
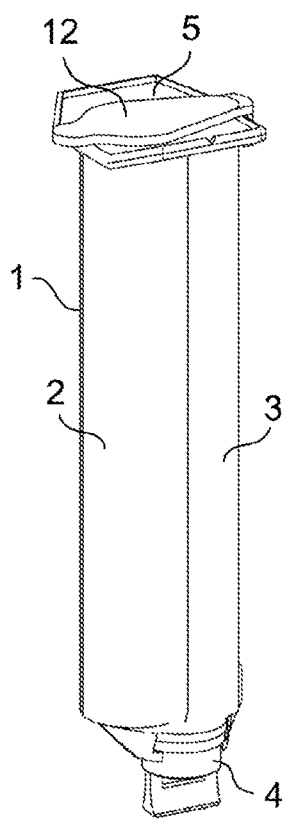
FIG. 3 schematically illustrates a double-barrelled syringe of the type used in the present invention with an additional temporary sealant means, or barrier, located on the distal end.

From FIG. 2, one can appreciate that when plunger, item 10, is inserted, pistons, items 6 and 8, are forced in the direction of mixing element, item 11, that is used to substitute the removable cap, item 4, when the adhesive is being dispensed. From FIGS. 1 and 2 it may be emphasized that the distal end of the syringe body is open to enable insertion of the plunger and that the pistons are freely movable to allow contents to be dispensed through the mixer. Commercial double-barrelled syringes currently do not have a temporary sealing means on the non-product side of the pistons.

Bulk Composition

The bulk composition comprises two parts, which are contained in a double-barrelled syringe: Part A is a cyanoacrylate based adhesive composition and Part B is a composition comprising a mixture of plasticizer and catalyst, or non-CA monomer mixture-catalyst, and it may contain further components depending on the final use of the adhesive.

The two parts react together when mixed to cure the bulk product and so must be stored separately, for example in separate chambers of a double-barrelled syringe as in the present invention.

The adhesive part is CA based and preferably derived from either lower alkyl ($C_1$-$C_4$) ester type cyanoacrylates, such as ethyl cyanoacrylate (ECA), or mixtures thereof with alkoxylalkyl based cyanoacrylates, such as methoxyethyl cyanoacrylate (MECA). The ECA monomer has a high vapour pressure and is known to generate white staining ('blooming') when its polymerized vapours condense on substrates—most noticeably on dark coloured or transparent substrates.

Examples of 2KCA bulk compositions based on either type of monomer are disclosed, for example, in PCT/162014/065530 and in European patent application EP-A-14382343.

Typically such adhesive Part A is a gel showing a viscosity of at least 50,000 cps at room temperature (Brookfield, Spindle 14 at 1.5 rpm).

Part B for bulk products commonly comprises plasticizers and catalysts and may contain fillers and again it is disclosed, for example, in PCT/162014/065530. The viscosity of Part B is generally matched to within the same range as the adhesive of Part A in order to get a uniform mixing before use.

Part B for bulk products comprising non-CA monomer mixtures and catalysts is disclosed, for example, in WO-A-2012/035112. The non-CA monomer component may be selected, for example, from an epoxy component, an episulfide component, an oxetane component, a vinyl ether component and combinations thereof, or methacrylate or acrylate components or mixtures thereof as disclosed in, for example, WO-A-2013/111036 or U.S. Pat. No. 3,940,362, or it may contain styrene derivatives, as disclosed, for example, in U.S. Pat. No. 3,282,773.

First Physical Part of Primary Inner Pack

The first physical part of the primary inner pack is a removable, re-closable cap schematically illustrated by item 4 in FIG. 1. This cap, which covers the orifices, is used to dispense product from the primary inner pack and seals the product at least at the proximal end of the primary pack, protecting the product between uses. Examples of such removable caps for double-barrelled syringes are disclosed, for example, in International patent application WO-A-2005075312. Removable or re-closable caps are designed for re-use during storage and are not for temporary use, for example during display of the product before purchase.

Second Physical Part of Primary Inner Pack

Second physical part of primary inner pack refers to the group of two pistons located in the chambers of double-barrelled syringes such as those represented schematically in FIG. 1, items 6 and 8. In FIG. 1, the pistons illustrated are of different diameter and have O-rings shown as items 7 and 9. However O-rings may be removed. Volumetric ratios of 1:1, 2:1, 4:1, 10:1 (Part A:Part B) are commonplace for syringe primary packs, so pistons have corresponding diameters. The cyanoacrylate based adhesive composition (Part A) is generally present in an equal or greater volume to the plasticizer-catalyst (Part B) of the composition. Preferably the piston in Part A does not have an O-ring. The O-ring on the piston of the second chamber FIG. 1, item 3, is optional and is not needed when the viscosity of Part B is high. Examples of such pistons are disclosed, for example, in International patent applications WO-A-99/44907, WO-A-01/56894, WO-A-2005/075312, and WO-A-2007/004203.

Temporary Sealing Means

The temporary sealing means forms a barrier between volatile constituents emitted by the bulk composition and the outer secondary pack, and which means are located between the second physical part and the distal end of the syringe.

The temporary sealing means is either:
  partially confined within the primary inner pack and separated from the second physical part by a gap and is a bung or cap, or,
  confined within the primary inner pack, but in initial intimate contact with the second physical part, it is not in intimate contact with the bulk composition, and is a grease, wax, or cured sealant, or,
  adhered or shrunk-wrapped across the open end of the primary inner pack as a non-permeable tape or film.

In a preferred embodiment the temporary sealing means is either:
  partially confined within the primary inner pack and separated from the second physical part by a gap and is a bung or cap, or,
  confined within the primary inner pack but in initial intimate contact with the second physical part, it is not in intimate contact with the bulk composition, and is a grease, wax, or cured sealant.

In another preferred embodiment the temporary sealing means is either:
  partially confined within the primary inner pack and separated from the second physical part by a gap and is a bung or cap, or,
  adhered or shrunk-wrapped across the open end of the primary inner pack as a non-permeable tape or film.

In another preferred embodiment the temporary sealing means is either:
  confined within the primary inner pack but in initial intimate contact with the second physical part, it is not in intimate contact with the bulk composition, and is a grease, wax, or cured sealant, or,
  adhered or shrunk-wrapped across the open end of the primary inner pack as a non-permeable tape or film.

Figure 4:
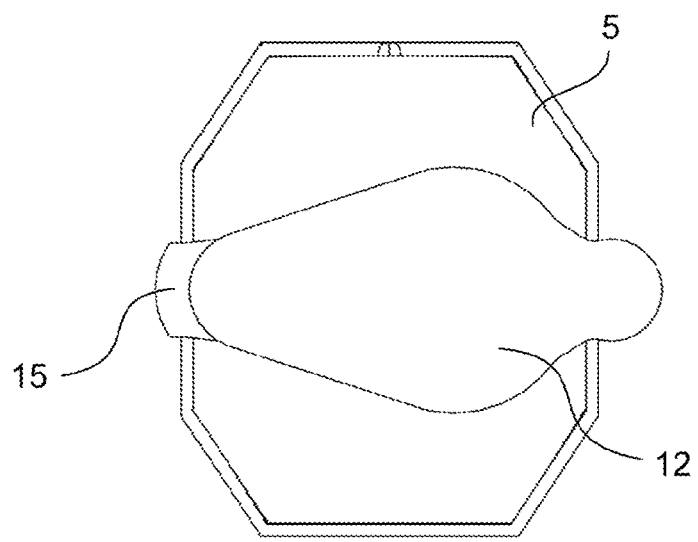
FIG. 4 represents an example of a temporary sealant means, or barrier, used to seal a double-barrelled syringe in plan view.
Figure 5:
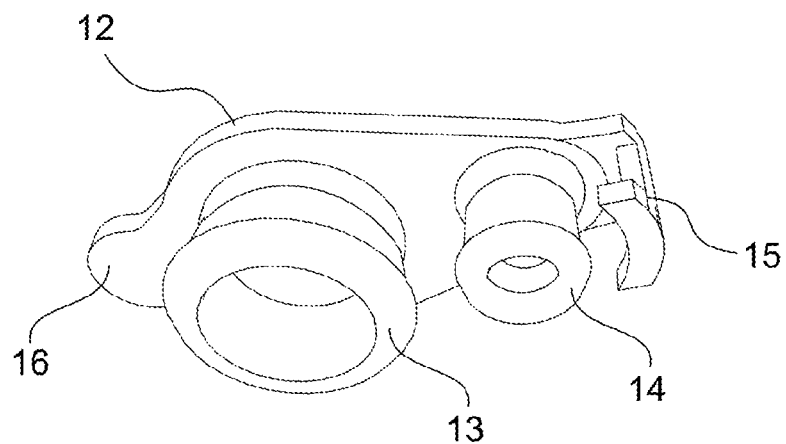
FIG. 5 shows an example in magnified view of a temporary sealant means, or barrier for a double-barrelled syringe.

In a specially preferred embodiment, the temporary sealing means are in the physical form of a bung or cap for the filled double-barrelled syringe. The bung or cap may act as a barrier only for the CA adhesive containing chamber of the double-barrelled syringe. A second bung may be added to the plasticizer-catalyst or non-CA monomer-mixture-catalyst side if considered necessary. Alternatively a bung or cap can seal-off both chambers of the double-barrelled syringe in the form of a double bung or cap. A schematic representation of the latter option is shown in FIGS. 4 and 5. FIG. 4 shows a view from above illustrating the bung or cap, item 12, placed so as to seal the distal end of the syringe and FIG. 5 shows a magnified example of a suitable bung or cap of the invention with male protrusions, items 13 and 14, that may be inserted into the respective chambers of a double-barrelled syringe, items 2 and 3 of FIG. 1. Even if it is unnecessary to seal the plasticizer-catalyst chamber, because these components of the composition do not have volatile constituents that cause staining of the secondary outer pack, the double bung or cap design make for robust, ergonomically practical and aesthetically pleasing parts. The bung or double bung may optionally have a pull-off tab indicated by item 16 in FIG. 5, and an optional end clip, item 15.

Bungs or caps may be constructed from a variety of different materials provided they are impermeable to vapours and provide a tight seal and are thus preferably somewhat deformable. Examples of suitable materials are soft PVC, silicones, synthetic thermoplastic vulcanizates, and synthetic or natural rubber compositions. Preferably the bung or cap is easy to insert after syringe filling and easy to remove when the plunger is to be inserted before use of the adhesive composition.

Figure 6:
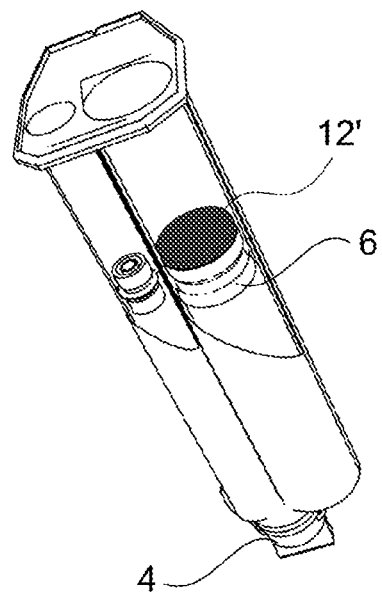
FIG. 6 schematically illustrates a double-barrelled syringe of the type used in the present invention with an alternative type of temporary sealant means, or barrier to that shown in FIG. 3.

In another specially preferred embodiment illustrated in FIG. 6 the temporary sealing means is a grease, wax or sealant that is applied atop one (e.g. item 12' in FIG. 6) or both pistons in a filled double-barrelled syringe containing the composition with at least one volatile constituent. Sealant materials may be derived from a flexible non-odour CA such as that described in EP-A-14382343 or fast curing silicone, provided manufacturing operations can be scheduled to permit the longer set times of such materials relative to the fast gelation or solidification of greases or waxes. Preferably the sealant is a cured cyanoacrylate or cured silicone composition. As with the bung or cap option, usually it is only necessary to temporarily seal the CA adhesive side (Part A) especially when the CA is ECA-based or has more than 0.5% weight/weight of ECA content in the adhesive composition. Greases, waxes and sealants should be sufficiently viscous to remain in intimate contact with the distal end-facing side of the piston or its periphery in the adhesive chamber of the double-barrelled syringe (Part A) and be of sufficient volume to create a barrier against emissions from volatile constituents of the composition such as ECA. The grease, wax, or sealant must stay in place during transport and storage and display conditions of the display pack especially if the display package experiences elevated temperatures, in which case the grease or wax should have a melting point above about 65° C. Most preferably grease, wax and sealants never contact bulk compositions, in contrast to the situation described in the '784 US patent, but instead contact only emissions from volatile constituents of the bulk compositions that permeate past the piston in the direction of the outer secondary pack. The grease, wax or sealant makes intimate contact with the second physical part (piston) on the distal facing side of the latter, but it does not adhere to it to any significant extent that would prevent movement of the piston away from its initial position. In this way a temporary seal is produced between the upper periphery of the piston and the inside wall of the adhesive containing syringe chamber. Common petrolatum jellies (Vaseline), silicone laboratory high vacuum greases, Baysilone™ Paste (Dow Corning, Bayer respectively), high temperature greases (Silkolene™ RG2), microcrystalline waxes (IGI Microsere™) are ideally suited and may be dispensed most rapidly as molten liquids in volumes in the range of 0.2 to 3 mL, more preferably 0.5 to 2 mL and most preferably 0.75 to 1.5 mL, after the syringe is filled. The temporary sealant material gels or solidifies quickly in a matter of seconds sealing the primary pack before it is placed into the outer secondary pack.

In another specially preferred embodiment, the temporary sealing means is provided as non-permeable tape or film adhered or shrunk-wrapped across the open end of the primary inner pack. In this case the temporary sealing means is provided in the following way: the distal end of the syringe are shrink-wrapped with film that is impervious to emissions of volatile constituents from the composition, or a similarly non-permeable pressure sensitive adhesive tape is used to seal the syringe and prevent staining of the secondary pack. Suitable tapes are, for example, Patex® Power Tape.

Temporary sealing means is used to avoid the problem of the white staining due to the polymerization of CA vapours in the packaging from the manufacture of the syringe comprising the adhesive composition up to the use by the final consumer. The display pack of the present invention, comprising temporary sealing means for the CA composition is maintained free of staining due to CA vapours.

Next, several examples of the invention are provided for illustrative but not limitative purposes.

EXAMPLES

Preparative Example: Preparation of a Cyanoacrylate Based Adhesive Composition

A cyanoacrylate based adhesive composition was prepared according to the components shown in Table 1, which is the so-called Part A of the bulk composition:

TABLE 1

| Component | Function | % by weight |
|---|---|---|
| Ethyl cyanoacrylate | Polymerizable monomer | 87.563 |
| Methyl polymethacrylate (Degacryl ® M-449, Evonik) | Thickener | 5.98 |
| Hydrophobized silica (Aerosil ® R 202, Evonik) | Thixotropic agent | 5.98 |
| Crown ether 18-6 (18 Crown 6, Alfa Aesar Co.) | Accelerator | 0.2 |
| Methylene-bis-(4-methyl-6-t-butylphenol) | Antioxidant | 0.22 |
| 4-methoxyphenol | Radical stabilizer | 0.04 |
| Methanesulfonic acid | Stabilizer | 0.016 |
| Sulfur dioxide | Stabilizer | 0.001 |

In a similar way a plasticizer-catalyst composition was prepared as described by Table 2, which is the Part B of the bulk composition:

TABLE 2

| Component | Function | % by weight |
|---|---|---|
| Triacetin | Plasticizer/Diluent | 92.25 |
| Hydrated calcium silicate (Promaxon ® D, Lapinus Fibers) | Heterogeneous initiator | 3.69 |
| Caffeine | Anionic initiator | 0.37 |
| Hydrophobized silica (Aerosil ® R 202, Evonik) | Thixotropic agent | 3.69 |

Parts A and B together form the bulk composition. Part B has no volatile constituents that cause staining of secondary outer packs. ECA monomer has a high vapour pressure, is volatile and is known to cause white staining (blooming) when its vapours condense and polymerize on surfaces.

Example 1: Test with a PVC Fitting as Sealing Temporary Means

A 500 ml volume heavy walled transparent glass jar with a tightly stopped lid was used to simulate a transparent secondary pack. Double-barrelled syringes of the Sulzer Mixpac—K-series were used as kits with end stoppers and pistons. Pistons used to confine adhesive compositions containing volatile constituents did not have O-rings. O-rings were left only on pistons for plasticizer-catalyst compositions.

Syringes to be tested were first assembled with pistons, which were pushed fully toward the proximal end of the two chambers 2 and 3 in FIG. 1. The syringes were then filled 'through-the-nose' by simultaneously forcing the compositions denoted Part A and Part B, prepared according to the Preparative example, through the dispensing orifices against the pistons in the respective chambers, the latter moved in a direction opposite to the incoming flow of compositions, to an intermediate full position in the syringe chambers. Syringe filling requires use of a specialised semi-automatic filling machine. Syringes tested were of the 10 g size and Part A to Part B volumetric ratios were 4:1 (A:B).

A tight fitting PVC bung Moss Pull Plugs (Essentra Components) was inserted into chamber containing the adhesive Part A in the filled syringe.

The removable cap, item 4 of FIG. 1, was then tightly closed after the filling operation.

The filled syringe was held vertically in a small beaker put inside the glass jar so the distal end of the syringe was pointing upwards. One drop of neat DBU (diazabicycloundecene, Sigma-Aldrich) was added to the base of the glass jar by pipette. The presence of this volatile amine exaggerates staining ("blooming"), as disclosed in Tathouh et al., J. Polymer Sci.: Part A: Polymer Chemistry, 49, 257, 2100. Afterwards, the jar was tightly stoppered. The thus assembled test sample was placed in an oven at 55° C. for 60 minutes, then removed and allowed to cool to room temperature (about 25° C.).

No staining whatsoever was evident after the test, or repeated tests conducted with heating for several hours or even overnight. When the jar was opened only DBU amine vapour could be detected.

Example 2: Test with a High Melting Point Wax as Sealing Temporary Means

The method disclosed in Example 1 was repeated in an analogous way, wherein in the present example wax (IGI Microsere™ 5714A) showing a melting point of approx. 80° C. was melted and 3 mL applied atop the piston confining adhesive Part A in the filled syringe as illustrated by item 12' in FIG. 6 before confining the sample in the jar and exposing it to temperature.

No staining whatsoever was evident after the test, or repeated tests conducted with heating for several hours or even overnight. When the jar was opened only DBU amine vapour could be detected. This test result was identical to that of Example 1.

Example 3: Test with a Tight Fitting Double-Bung as Sealing Temporary Means

The method disclosed in Example 1 was repeated in an analogous way, wherein in the present example a tight fitting double-bung specially produced by 3D-printing of plastic PLA and designed as shown in FIG. 5 was inserted into both chambers of a filled double-barrelled syringe containing the adhesive Part A and the plasticizer-catalyst Part B before confining the sample in the jar and exposing it to temperature.

No staining whatsoever was evident after the test, or repeated tests conducted after heating for several hours or even overnight. When the jar was opened only DBU amine vapour could be detected. This test result was identical to that of Example 1.

Example 4: Tests in a Sealed Transparent Plastic Bag

Examples 1, 2 and 3 were repeated by replacing the glass jar with a sealed transparent plastic bag, which was used as a secondary outer pack. It was subjected to a heating at no more than 40° C.

No staining was evident inside the plastic bags after the test on prolonged storage.

Example 5: Tests in a Sealed Transparent Plastic Clamshell Pack

Examples 1, 2 and 3 were repeated by replacing the glass jar with a sealed transparent plastic clamshell pack, which was used as a secondary outer pack. It was subjected to a heating at no more than 40° C.

No staining was evident inside the clamshell packs after the test on prolonged storage.

Example 6: Tests in Closed Foldable Box

Examples 1, 2 and 3 were repeated by replacing the glass jar with a closed foldable, which was used as a secondary outer pack. It was subjected to a heating at no more than 40° C.

No staining was evident inside the foldable box after the test on opening.

Example 7: Tests Using a Heavy Industrial Pressure Sensitive Adhesive Tape

Examples 1 and 4 were repeated except a heavy industrial pressure sensitive adhesive tape was applied across the open chambers at the distal end of the filled syringe, which was subjected to the same conditions as in the general method.

No discernible staining of the secondary pack was evident after the test or upon storage.

Comparative Example 1: Test without Sealing Temporary Means in a Glass Jar

A sample was prepared according to the general method described in Example 1, but without using any temporary sealing means for the syringe comprising Part A.

Copious quantities of heavy white staining were easily discernible on the inside walls of the bottle after the test. When the bottle was opened ECA vapour was noticeable by smell as was the amine DBU.

Comparative Example 2: Test without Sealing Temporary Means in a Sealed Transparent Plastic Bag A further sample was prepared according to the general method described in Example 1 with the following differences: no temporary sealing means were used for the syringe components, a sealed transparent plastic bag was used as a secondary outer pack in place of the glass bottle, and heating was carried out at no more than 40° C.

Copious quantities of heavy white staining were easily discernible after the test on the inside of the sealed transparent plastic bag.

Comparative Example 3: Test without Sealing Temporary Means in a Sealed Transparent Plastic Clamshell Pack A further sample was prepared according to the general method described in Example 1 with the following differences: no temporary sealing means were used for the syringe components, a transparent plastic clamshell pack was used as a secondary outer pack in place of the glass bottle, and heating was carried out at no more than 40° C.

Copious quantities of heavy white staining were easily discernible on the inside of the sealed transparent clamshell pack after the test.

Comparative Example 4: Test without Sealing Temporary Means in a Cardboard Folding Box A further sample was prepared according to the general method described in Example 1 with the following differences: no temporary sealing means were used for the syringe composition, a folding box made of cardboard that was opaque was used as a secondary pack in place of the glass bottle, and heating was carried out at no more than 40° C.

White staining was discernible on the inside of the folding box once opened after the test. The (opaque) box was not as effective as the lidded glass jar at trapping vapours inside the secondary pack.

The invention claimed is:

1. A display package for 2K cyanoacrylate compositions, comprising:
   a secondary outer pack;
   a primary inner pack, which is a double-barrelled syringe that contains:
      a bulk composition comprising:
         Part A: a cyanoacrylate based adhesive composition; and
         Part B: a composition comprising a mixture of plasticizer and catalyst or a mixture of non-CA monomer and catalyst;
      two distinct physical parts; and
      temporary sealing means;
   a plunger; and
   one or more mixing elements,
   wherein
      the two distinct physical parts contact the bulk composition or its constituents,
      the first physical part located at one end of the primary inner pack is a removable cap which closes an orifice or orifices from where the bulk composition is dispensed,
      the second physical part at intermediate position within the primary inner pack is a group of two movable pistons which contact and confine the bulk composition between itself and the end of the primary inner pack where the orifice or orifices are located, and
      the temporary sealing means, which forms a barrier between volatile constituents emitted by the bulk composition and the secondary outer pack, and which means is located between the second physical part and the distal end of the syringe,
   wherein the temporary sealing means is a bung or cap partially confined within the primary inner pack and separated from the second physical part by a gap, or
   wherein the temporary sealing means is a grease, wax, or cured sealant confined within the primary inner pack but in initial intimate contact with the second physical part, and it is not in intimate contact with the bulk composition.

2. The display package according to claim 1, wherein the secondary outer pack is a foldable cardboard, a blister package or a bag.

3. The display package according to claim 1, wherein the secondary outer pack is transparent or has at least one transparent section.

4. The display package according to claim 1, wherein the secondary outer pack is a blister package.

5. The display package according to claim 1, wherein the secondary outer pack is a foldable cardboard box with a transparent plastic viewing panel.

6. The display package according to claim 1, wherein the cyanoacrylate based adhesive composition comprises lower alkyl ($C_1$-$C_4$) ester type cyanoacrylates, or mixtures thereof with alkoxylalkyl based cyanoacrylates.

7. The display package according to claim 1, wherein the temporary sealing means is a bung or cap partially confined within the primary inner pack and separated from the second physical part by a gap.

8. The display package according to claim 1, wherein the temporary sealing means is a grease, wax, or cured sealant confined within the primary inner pack but in initial intimate contact with the second physical part, and it is not in intimate contact with the bulk composition.

9. The display package according to claim 1, wherein the secondary outer pack forms a stand.

10. The display package according to claim 1, wherein the secondary outer pack has a hook-hole to allow the display to be hung or hook.

* * * * *